(12) United States Patent
Ruman et al.

(10) Patent No.: US 6,976,978 B2
(45) Date of Patent: Dec. 20, 2005

(54) REFASTENABLE PULL-ON TRAINING PANT WITH DIAGONAL SEAMS

(75) Inventors: Marcille Faye Ruman, Oshkosh, WI (US); Kathleen Irene Ratliff, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 102 days.

(21) Appl. No.: 10/056,888

(22) Filed: Jan. 25, 2002

(65) Prior Publication Data

US 2002/0112276 A1 Aug. 22, 2002

Related U.S. Application Data

(63) Continuation-in-part of application No. 09/790,340, filed on Feb. 22, 2001.

(51) Int. Cl.⁷ .............................................. A61F 13/15
(52) U.S. Cl. .................. 604/385.01; 604/386; 604/394
(58) Field of Search .................. 604/385.01, 386–392, 604/394–396

(56) References Cited

U.S. PATENT DOCUMENTS

| | | | |
|---|---|---|---|
| 2,545,216 A * | 3/1951 | Toussie | 604/394 |
| 2,545,674 A * | 3/1951 | Ralph | 604/394 |
| 2,591,079 A * | 4/1952 | Leaton | 604/386 |
| 2,664,895 A * | 1/1954 | Shulman | 604/366 |
| 2,834,347 A * | 5/1958 | Connally | 604/389 |
| 3,039,466 A * | 6/1962 | Wilson | 604/398 |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,559,648 A * | 2/1971 | Mason, Jr. | 604/375 |
| 3,692,618 A | 9/1972 | Dorschner et al. | |
| 3,802,817 A | 4/1974 | Matsuki et al. | |
| 3,849,241 A | 11/1974 | Butin et al. | |
| 4,205,679 A | 6/1980 | Repke et al. | |
| 4,315,508 A | 2/1982 | Bolick | |
| 4,340,563 A | 7/1982 | Appel et al. | |
| 4,372,311 A | 2/1983 | Potts | |
| 4,663,220 A | 5/1987 | Wisneski et al. | |
| 4,704,116 A | 11/1987 | Enloe | |
| 4,940,464 A | 7/1990 | Van Gompel et al. | |
| 4,944,734 A | 7/1990 | Wallach | |
| 4,952,550 A | 8/1990 | Wallach et al. | |
| 5,046,272 A | 9/1991 | Vogt et al. | |
| 5,062,839 A * | 11/1991 | Anderson | 604/385.21 |
| 5,104,116 A | 4/1992 | Pohjola | |
| 5,110,390 A | 5/1992 | Martini et al. | |

(Continued)

FOREIGN PATENT DOCUMENTS

EP 217 032 B1 2/1992

(Continued)

Primary Examiner—Larry I. Schwartz
Assistant Examiner—C. Lynne Anderson
(74) Attorney, Agent, or Firm—Pauley Petersen & Erickson (57) ABSTRACT

A disposable pant garment is made from a web by joining front and back side panels attached to the garment chassis. The side panels have diagonal edges in order to result in side seams on the garment which run diagonally on the garment side. This diagonal side seam provides superior fit and releasability, especially in the case of refastenable side seams such as may be used for training pants. One or more of the side panels may be constructed from a plurality of pieces.

22 Claims, 9 Drawing Sheets

U.S. PATENT DOCUMENTS

| | | |
|---|---|---|
| 5,224,405 A | 7/1993 | Pohjola |
| 5,226,992 A | 7/1993 | Morman |
| 5,283,090 A | 2/1994 | Umemura |
| 5,386,595 A | 2/1995 | Kuen et al. |
| 5,509,913 A | 4/1996 | Yeo |
| 5,897,545 A | 4/1999 | Kline et al. |
| 5,939,467 A | 8/1999 | Wnuk et al. |
| 5,957,908 A | 9/1999 | Kline et al. |
| 6,063,914 A | 5/2000 | Wolf et al. |
| 6,443,940 B1 * | 9/2002 | Ashton et al. .............. 604/396 |

FOREIGN PATENT DOCUMENTS

| | | |
|---|---|---|
| EP | 1 174 103 | 1/2002 |
| JP | 9066071 | 3/1997 |
| WO | WO 99/60969 | 12/1999 |
| WO | WO 99/60970 | 12/1999 |
| WO | WO 99/60974 | 12/1999 |
| WO | WO 00/23025 | 4/2000 |
| WO | WO 00/37005 | 6/2000 |
| WO | WO 00/37009 | 6/2000 |

* cited by examiner

REFASTENABLE PULL-ON TRAINING PANT WITH DIAGONAL SEAMS

CROSS REFERENCE TO RELATED APPLICATION

This application is a continuation in part application of application Ser. No. 09/790,340 filed on 22 Feb. 2001.

BACKGROUND OF THE INVENTION

In the known art, there have been two ways of making an absorbent garment web into point of sale items. One is to put refastenable tabs, such as adhesive tape or hook and loop combinations onto the garment body, in the manner of an infant diaper, for later use to secure the back panel of the diaper to the front panel. A second is to bond the side edges of the front and back sections together to make a fixed waist band, in the manner of a training pant which is slid on and off the wearer like underwear. To remove such a garment if it becomes soiled it is necessary to destroy the side seam or tear the side panel in order to remove the garment like a diaper, as convenience and hygiene would dictate.

Designs for known fasteners and side seams have usually been vertically oriented, i.e., the zone of contact between the cooperative fasteners, or side seams, has typically been parallel to, or along, the long axis of the wearer, i.e., running from waist band to leg hole. This has made economic sense because the fasteners, or side seams, are applied parallel to the long axis of the garment chassis making for ease of automatic manufacturing.

However, these vertically oriented fastening seams suffer from some drawbacks. Such drawbacks include the fact that when the fastening seam is vertical, a large force may be necessary to open the seam, which can be inconvenient. An opening of a vertical seam along its wide dimension, i.e., from front to back when the seam is vertical, requires force applied to a greater surface area of the seam than necessary. Also, opening such a seam from the top is difficult without introducing lateral motion, e.g., front to back. The introduced lateral motion tends to pull the released portion of the seam both out and back as the separation continues, resulting in a wider surface area of separation and thus a greater required force. Also the seam area may be subjected to undue stress during removal or fastener disengagement. This stress can result in a tearing away of the fastener mechanisms from the underlying garment structure, or even tearing of the garment structure itself, especially in the case of hook and loop fasteners which can increase engagement bond strength over time.

Further, the known cooperative refastenable structures are designed to be fastened at the front, side, or back of the garment. Fastening engagement at the back of the garment is typically awkward in terms of finding and engaging the fasteners especially when, e.g., applying or reapplying a diaper or training pant to a squirming infant. Fastening integrity at the front of the garment is adversely affected by stresses incurred from leg movements that bend and pivot the garment. Further, due to leg movement stresses, front fastening often increases the incidence of red marks and an undesirably tight fit of the garment across the upper thigh.

There is therefore a desire for a seam, such as a hook and loop refastenable seam, that is easier to open, by encouraging separation of the seam material along its narrow dimension while moving progressively down the wide dimension; for example, tearing open the seam from top to bottom, or bottom to top, when the seam is vertical.

SUMMARY OF THE INVENTION

A diagonal seam of the present invention will promote the desired method of opening the seam along the narrowest dimension of the strip, thereby requiring less exertion of force and aligning the natural motion of seam disengagement, which is diagonal, with the seam of the garment. The present invention provides a disposable pant garment with diagonal side seams constructed by joining front and back side panels on each side of the garment together. The side panels have their distal edges, i.e., those edges farthest from the main body, or chassis, of the garment, formed at congruent angles to the longitudinal axis of the garment chassis.

In a particular embodiment both front and back side panels of the laid open garment have their distal edges angled from a back region of the garment to a front region of the garment. Particularly, a line or vector drawn from the leg opening edge to the waist opening edge of a front side panel along the distal edge will intersect the longitudinal axis of the chassis at an acute angle. A line, or vector drawn from the waist opening edge to the leg opening edge of a back side panel along its distal edge will also intersect the longitudinal axis at an acute angle congruent with the angle of the front side panel distal edge. When these side panels are joined, such a construction provides a side seam running on a diagonal from the upper front to the lower back across the side area of the garment. Each side seam is preferably easily detachable or releasably engaged. Detachability or releasability may be provided, e.g., by a weak bond between the panels which is designed to be separated with manual force, or by providing a line of weakness along the bonding area between the front and back side panels. The seam may alternatively be made refastenable through the use of cooperative fasteners which are selectively releasable, such as hook and loop, or adhesive arrangements, placed on opposing surfaces of the side panels to be joined during garment construction.

In particular embodiments it may be desirable for the side seams to be prefastened before being packaged for sale so that the wearer may don the garment in the regular manner of nondisposable pants.

DEFINITIONS

Within the context of this specification, each term or phrase below will include the following meaning or meanings.

"Article" refers to a garment or other end-use article of manufacture.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Congruent" refers to angles which fall within the same quadrant of Cartesian coordinates having a center point at the intersection of the longitudinal axis of the garment and the defined lines or vectors, and desirably within about plus minus thirty degrees of true congruency and more desirably within about plus minus five degrees of true congruency.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation. "Extensible" implies stretchability without recovery of the original size or shape.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearers body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Line of Weakness" is used to refer to a perforation, thinned area, nonpermanent or weak bond, or other means for facilitating separation of a material, a fabric or a layer of such material or fabric, whether defined by function or fabric type.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 3:
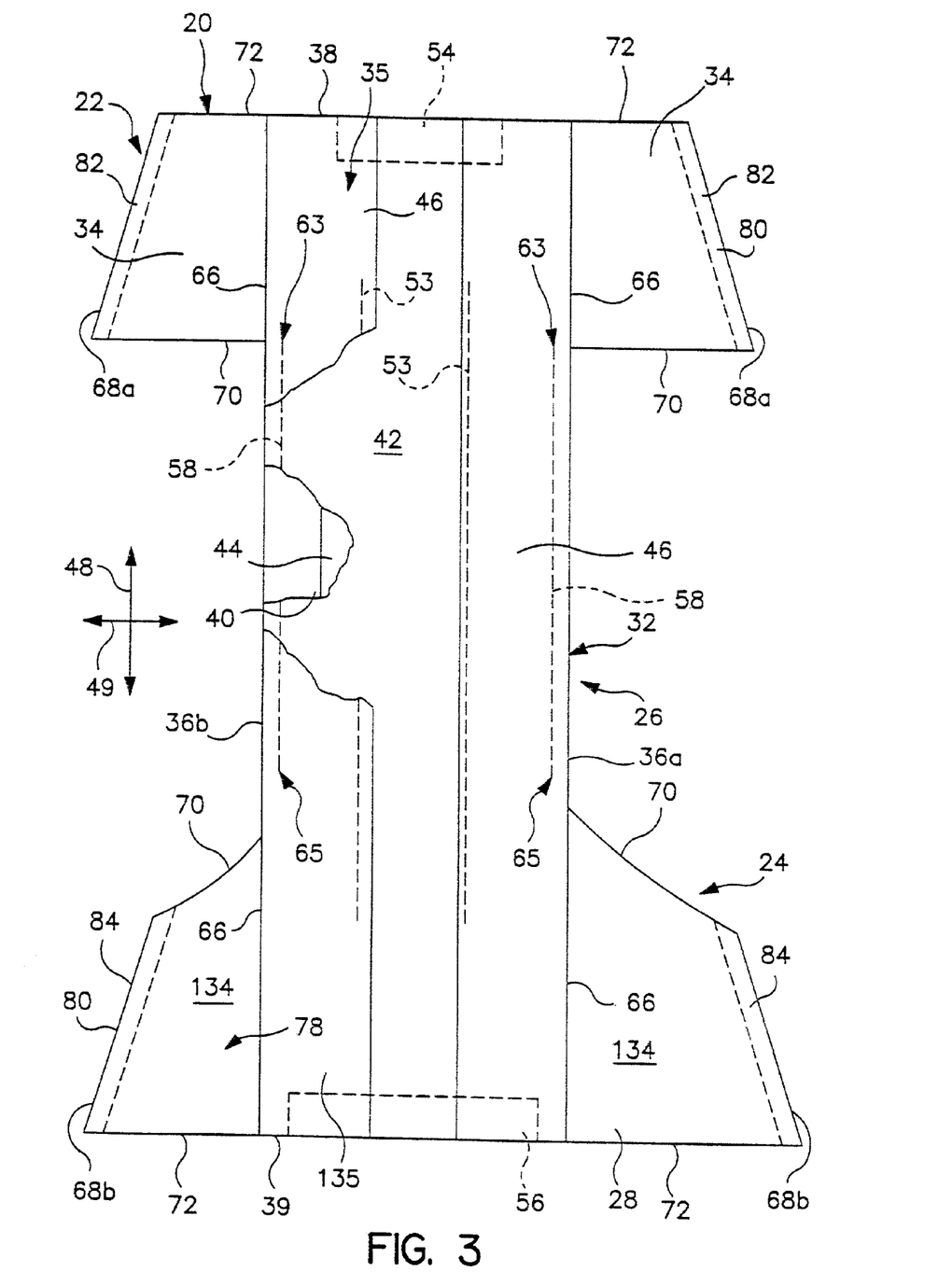
FIG. 3 is a plan view of an absorbent garment in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes depicted in FIG. 3. The longitudinal, or long, axis lies in the plane of the article and is generally parallel to a vertical plane that bisects a standing wearer into left and right body halves, when the article is worn. The transverse axis lies in the plane of the article generally perpendicular to the longitudinal axis. The article, although illustrated as longer in the longitudinal direction than in the transverse direction, need not be so.

"Machine direction" refers to the direction in which the web travels, as opposed to "cross direction" which refers a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a nonelastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be, and remain, bonded during normal use conditions of the absorbent garment.

"Polymers" include, but are not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements. The required separation force is typically beyond that encountered while wearing the absorbent garment.

Words of degree, such as "Substantially", "About", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The principles of the present invention can be incorporated into any suitable garment and especially disposable, or limited use garments. Examples of such suitable garments may include, but are not limited to, diapers, training pants, incontinence products, other personal care or health care garments, or the like. For ease of explanation, the description hereafter will be in terms of a child's training pant.

Figure 1:
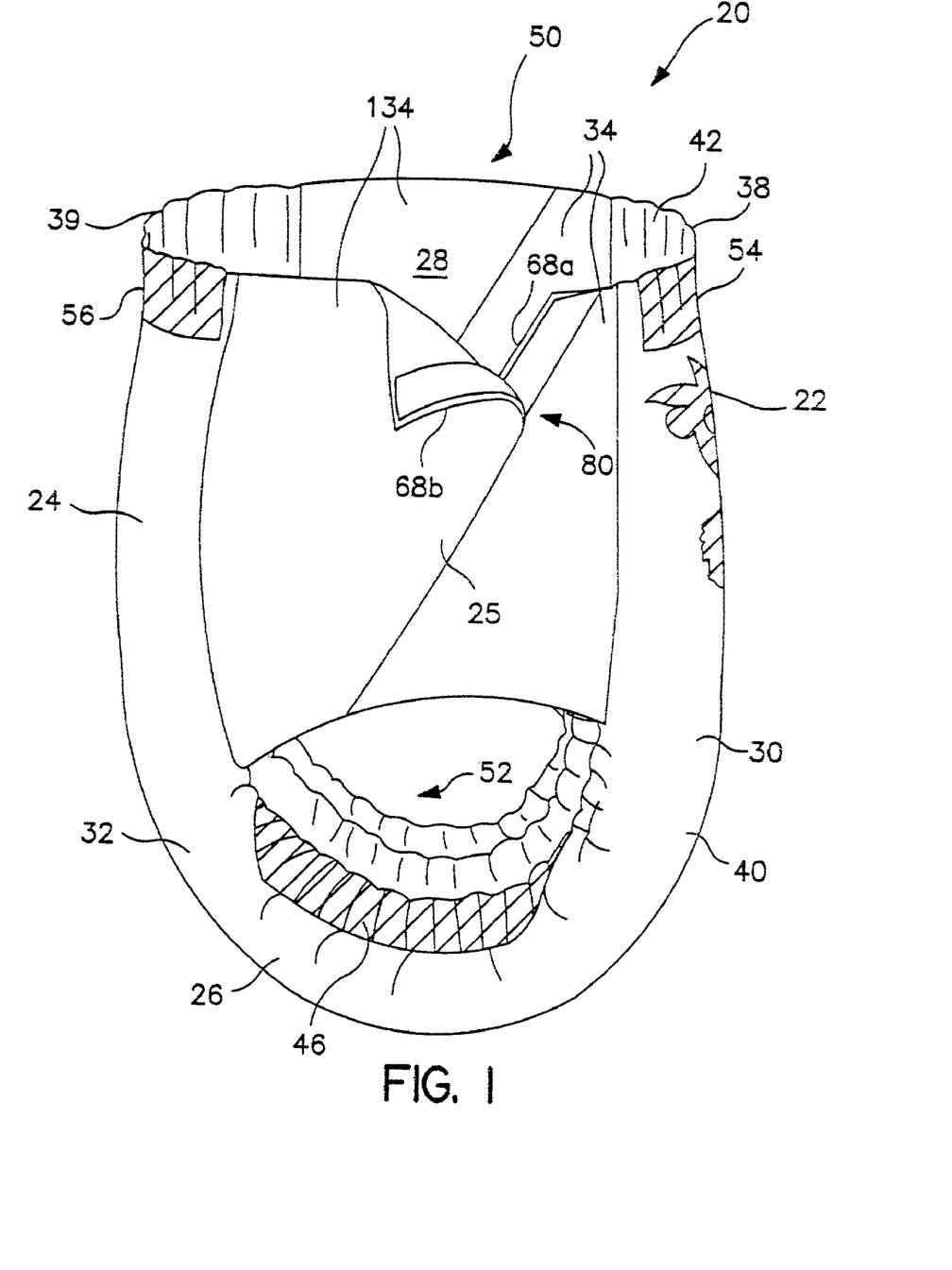
FIG. 1 is a side perspective view of an absorbent garment having refastenable side seams which are diagonal according to the present invention.
Figure 2:
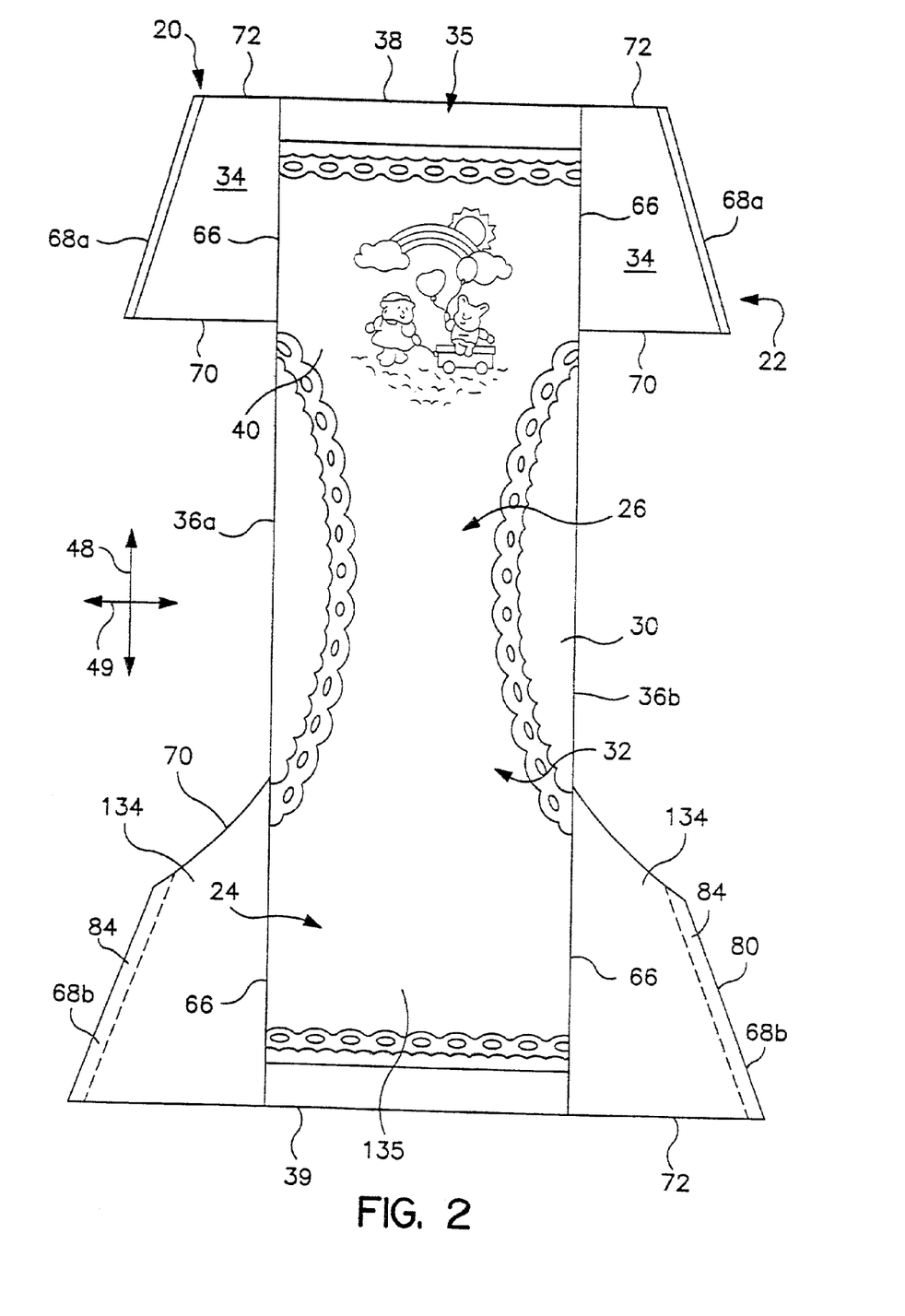
FIG. 2 is a plan view of an absorbent garment in a partially disassembled, stretched flat state, and showing the surface of the article that faces away from the wearer when the article is worn.

Referring to FIGS. 1–3, one such example of a disposable absorbent garment, such as a training pant 20, is illustrated for broad purposes of explanation of the materials and construction of the present invention. The training pant 20 includes an absorbent chassis 32 and a fastening system 80. The absorbent chassis 32 helps define for the training pant 20 a front region 22, a back region 24, a crotch region 26 interconnecting the front and back regions, an inner surface 28 which is configured to contact the wearer, and an outer surface 30 opposite the inner surface which is configured to contact the wearer's clothing. The absorbent chassis 32 also defines a pair of transversely opposed side edges 36a, 36b and a pair of longitudinally opposed waist edges, which are designated front waist edge 38 and back waist edge 39. The front region 22 is contiguous with the front waist edge 38, and the back region 24 is contiguous with the back waist edge 39.

The illustrated absorbent chassis 32 will have a pair of transversely opposed front side panels 34, and a pair of transversely opposed back side panels 134. The training pant 20 includes an outer cover 40, a bodyside liner 42 which is connected to the outer cover in a superposed relation, an absorbent assembly 44 (FIG. 3) which is located between the outer cover 40 and the bodyside liner 42, and a pair of containment flaps 46 (FIG. 3). For reference, arrows 48 and 49 depicting the orientation of the longitudinal axis and the transverse axis directions, respectively, of the training pant 20 are illustrated in FIGS. 2 and 3.

With the training pant 20 in the fastened position as partially illustrated in FIG. 1, the front and back regions 22 and 24, or front and back center panels 35, 135, are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

As shown, a refastenable seam 25 lies on a diagonal to the bilateral midline of a wearer and extends from the front region 22 at the waist opening 50 and downward to the rear region 24 at the leg edge opening 52. The natural, or preferred, hand motion of a caregiver in separating a side seam of a pant garment is from the front to the back of the garment and from the waist opening to the leg opening of the garment. By placing the refastenable seam to align with the natural hand motion of the caregiver, the opening force is generally applied only along the narrow dimension of the refastenable seam. Thus only the lowest requisite force for unfastening the side seam generally will be applied when opening the garment because the narrow dimension of the refastenable seam aligns with the natural removal motion. It is of course possible, although not as desirable, to orient the seam diagonally from the front region 22 at the leg opening 52 to the back region 24 at the waist opening 50.

The front region 22 of the absorbent chassis 32 includes the transversely opposed front side panels 34 and a front center panel 35 (FIGS. 2 and 3) positioned between and interconnecting the side panels, along with a front waist elastic member 54 and any other connected components. The back region 24 of the absorbent chassis 32 includes the transversely opposed back side panels 134 and a back center panel 135 (FIGS. 2 and 3) positioned between and interconnecting the side panels, as well as a rear waist elastic member 56 and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36a, 36b in the crotch region 26, along with leg end edges 70 of the side panels 34, 134, generally define the leg openings 52.

The absorbent chassis 32 is configured to contain and/or absorb any body exudates discharged from the wearer. For example, the absorbent chassis 32 desirably although not necessarily includes the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the transversely opposed side edges 36a, 36b and positioned in the crotch region 26 of the training pant 20. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bed-sheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may, but need not, have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbond web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, nonirritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44, if included in the garment, can be generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the absorbent chassis 32 in the respective front and back regions 22 and 24, and are releasably attached to one another by a fastening system 80. More particularly, as shown best in FIGS. 2 and 3, the front side panels 34 can be permanently bonded to and extend transversely beyond the transversely opposed side edges 36a, 36b of the absorbent chassis 32 in the front region 22 along attachment lines 66, and the back side panels 134 can be permanently bonded to and extend transversely beyond the transversely opposed side edges 36a, 36b of the absorbent chassis 32 in the back region 24 along attachment lines 66. The side panels 34 and 134 may be attached using attachment means known to those skilled in the art such as adhesive, thermal or ultrasonic bonding. The side panels 34 and 134 can also be formed as a portion of a component of the absorbent chassis 32, such as the outer cover 40 or the bodyside liner 42, as shown in FIG. 1.

In particular embodiments for improved fit and appearance, the side panels 34 and 134 desirably have an average length dimension measured parallel to the longitudinal axis direction 48 that is about 20 percent or greater, and particularly about 25 percent or greater, of the overall length dimension of the absorbent article, also measured parallel to the longitudinal axis. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 may have a continually decreasing length dimension moving from the attachment line 66 to a distal edge 68b of the back panel 134, as is best shown in FIGS. 2 and 3.

Figure 8:
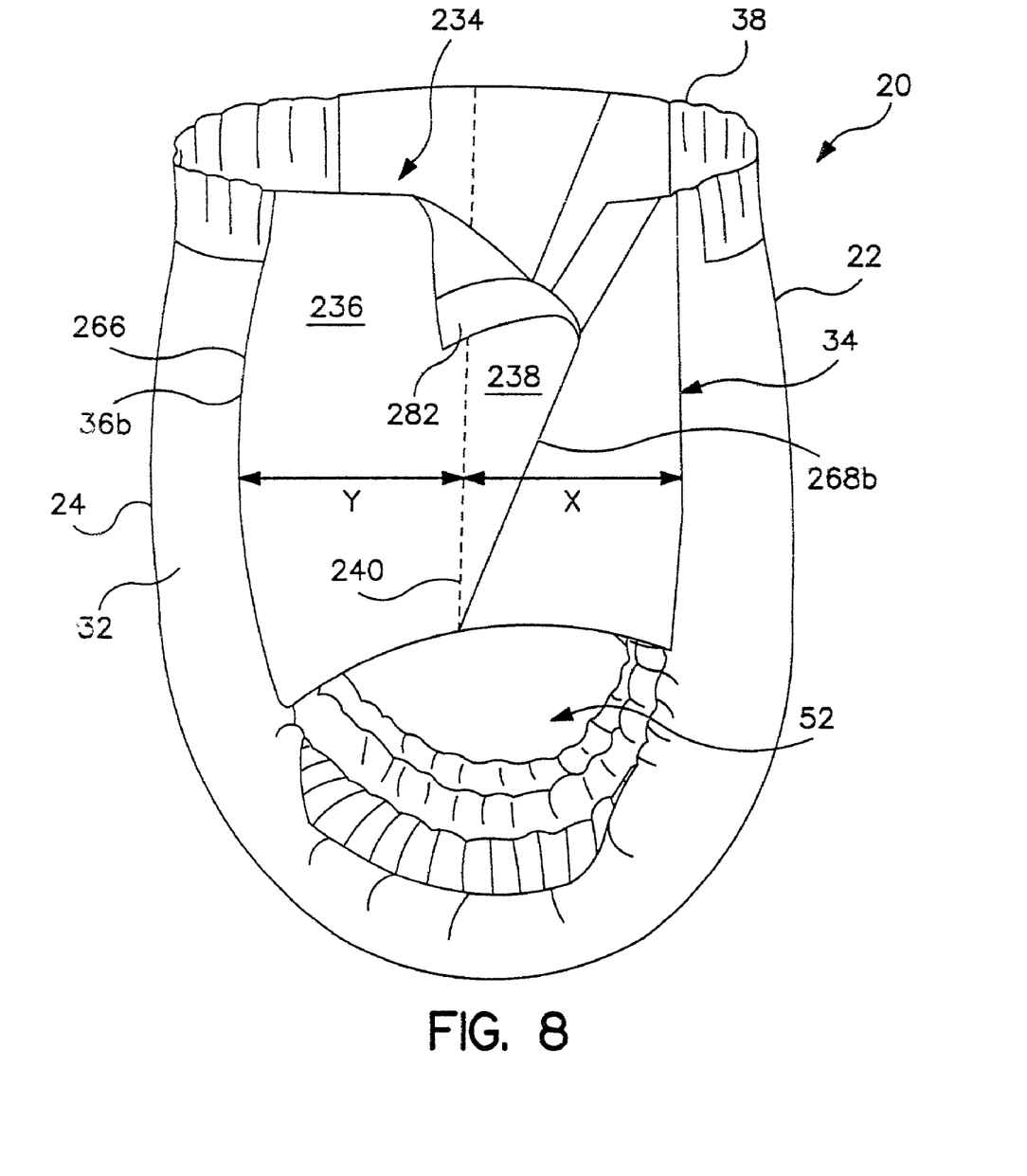
FIG. 8 is a side perspective view of an alternative absorbent garment having refastenable side seams which are diagonal according to the present invention and in which at least one of the front and back side panels is constructed from two panels with a bonded seam therebetween.
Figure 9:
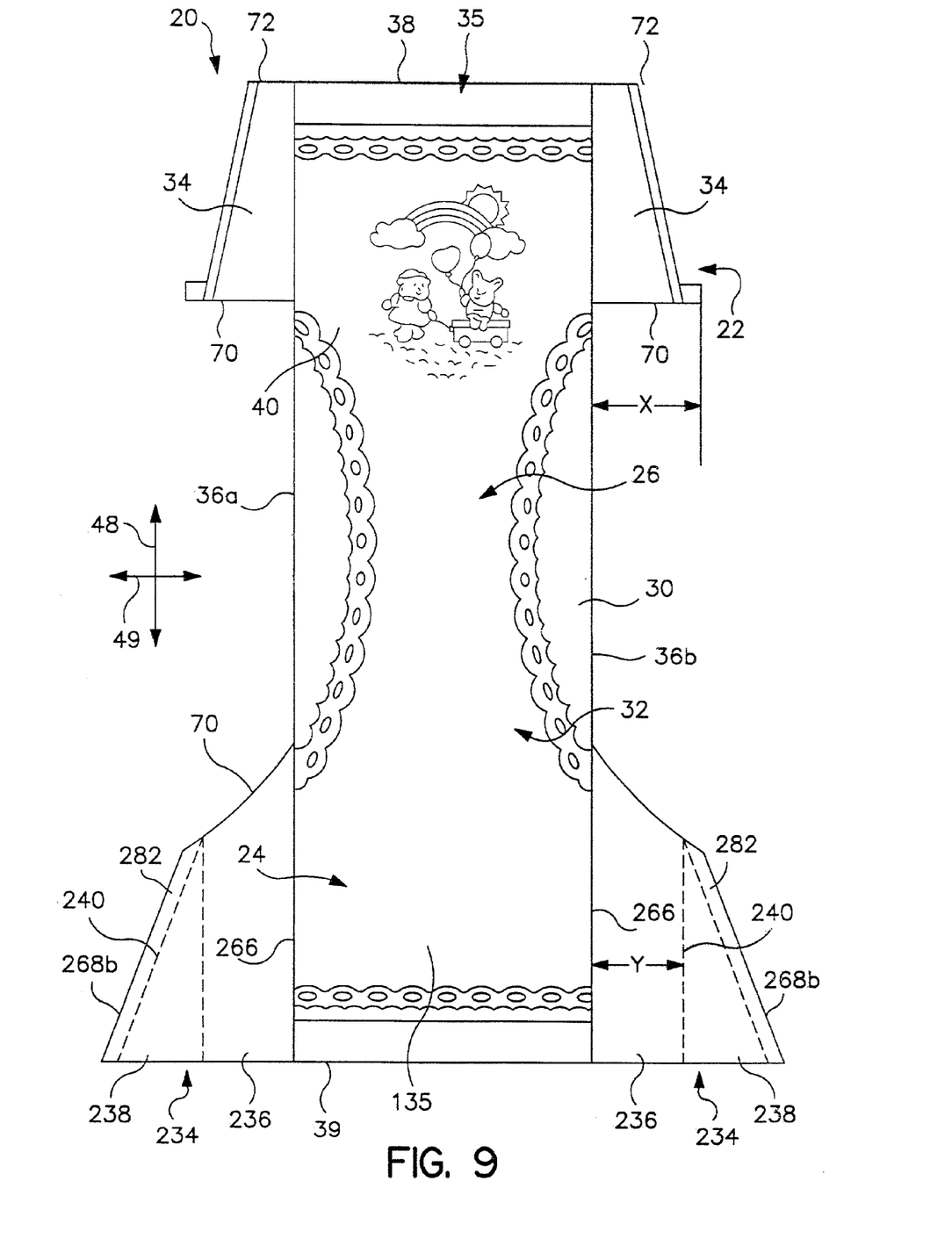
FIG. 9 is a plan view of the absorbent garment of FIG. 8 in a partially disassembled, stretched flat state, and showing the surface of the article that faces away from the wearer when the article is worn.

Each of the side panels 34 and 134 can include one or more individual, distinct pieces of material. In particular embodiments, one or more side panels can include first and second side panel portions that are joined at a seam. One or more of the portions may include an elastomeric material. For example, referencing FIGS. 8 and 9, an alternative aspect of the invention similar to FIGS. 1 and 2, but including multiple piece, or portion, side panels; shows a rear side panel 234 that includes two pieces 236, 238, proximal and distal to the absorbent chassis 32, respectively, joined by an ultrasonically bonded seam 240. The proximal side panel piece 236 is bonded to the absorbent chassis 32 at the side edge 36b along an attachment line 266. The distal piece 238 of the back side panel 234 has a diagonal distal edge 268b and carries a fastening component 282 for releasable attachment to the front side panel 34. The width of the proximal panel 236, i.e., from attachment line 266 to the ultrasonic bond 240 as indicated by "Y", is desirably approximately equal to the combined width of the front panel 34 and distal panel 238 when joined, as indicated by "X". The panels 34 and 234 are desirably, although not necessarily, configured so that the back side panel fastening component 282 exteriorly overlays at least a portion of the front side panel 34 when the two are fastened. Desirably, although not necessarily, the releasable fastening seam will extend diagonally from the waist edge 38 front side 22 of the garment 20 towards the back region 24 of the leg opening 52 as seen in FIG. 8. Desirably, the back side panel fastening element 282 will not extend over the ultrasonic bond 240. Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis direction 49 of the training pant 20. In particular embodiments, the front and back side panels 34 and 134 may each include an interior portion 78 disposed between a diagonal distal edge 68a, 68b and the respective front or back center panel 35 or 135. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al. Alternatively, the side panel material may include other woven or nonwoven materials, such as those described above as being suitable for the outer cover 40 or bodyside liner 42, or stretchable but inelastic materials.

The training pant 20 also includes a fastening system 80 for securing the training pant about the waist of the wearer (FIG. 1). The illustrated fastening system 80 includes fastening components 82 that are adapted to refastenably connect to mating, also sometimes called complementary or cooperating, fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped and may consist of a plurality of elements or may be integrated into the surface of the side panel. The fastening components 82 and the mating fastening components 84 are desirably aligned as strips of material proximal to and parallel with the diagonal distal edges 68a, 68b of the front and back side panels 34, 134, respectively.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a unidirectional hook pattern and having a thickness of about 0.089 millimeters (3.5 mils) and HTH-851 with a unidirectional hook pattern and having a thickness of about 0.051 millimeters (2 mils).

Figure 4:
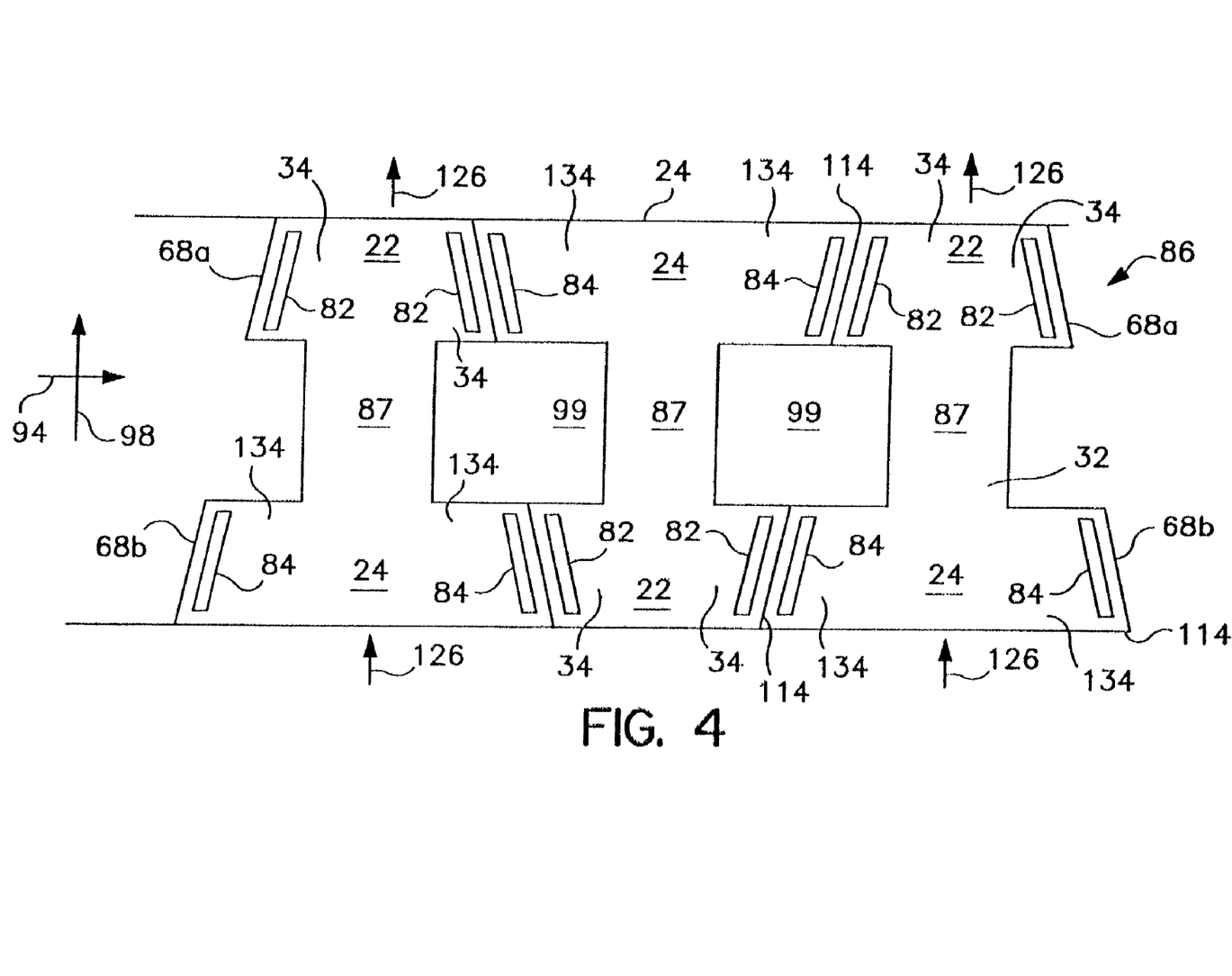
FIG. 4 shows in-process garments according to the present invention still attached to the manufacturing web, with the garments having their longitudinal axes in the cross direction of the web.

Referencing FIG. 4, a web 86 of in-process garments, collectively 87, has a machine direction 94 and a cross machine, or cross, direction 98. The garments 87 have their longitudinal axes 126 in the cross direction 98. Each garment 87 has a chassis portion 32 of generally rectangular shape and front and back side panel portions, collectively 34, 134, respectively, extending from the chassis portion. In the case of FIG. 4, the side panels 34, 134 and overall shape of the garment 87 are created by locating central cut-outs 99, or removable areas, in the middle of the web 86. While shown as rectangular or square, it will be appreciated that various shapes of cutouts 22 are possible. Individuated garments 128 (FIG. 8) according to the present invention having diagonal distal edges 68a, 68b of side panels 34, 134 are created at the appropriate point in the manufacturing process by individuating the garments with diagonal cuts 114 through the web 86. The cuts 114 are alternately positively and negatively sloped with respect to the longitudinal axis 126 of the garment 87. This results in side panel distal edges 68a, 68b which converge, from the back region 24 of the garment to the front region 22, towards the longitudinal axis 126. It will be noted by the artisan that adjacent garments have alternate front and back orientations on the web 86. Hook and loop fasteners, 82, 84 respectively, for the side panels 34, 134 are indicated schematically.

Figure 5:
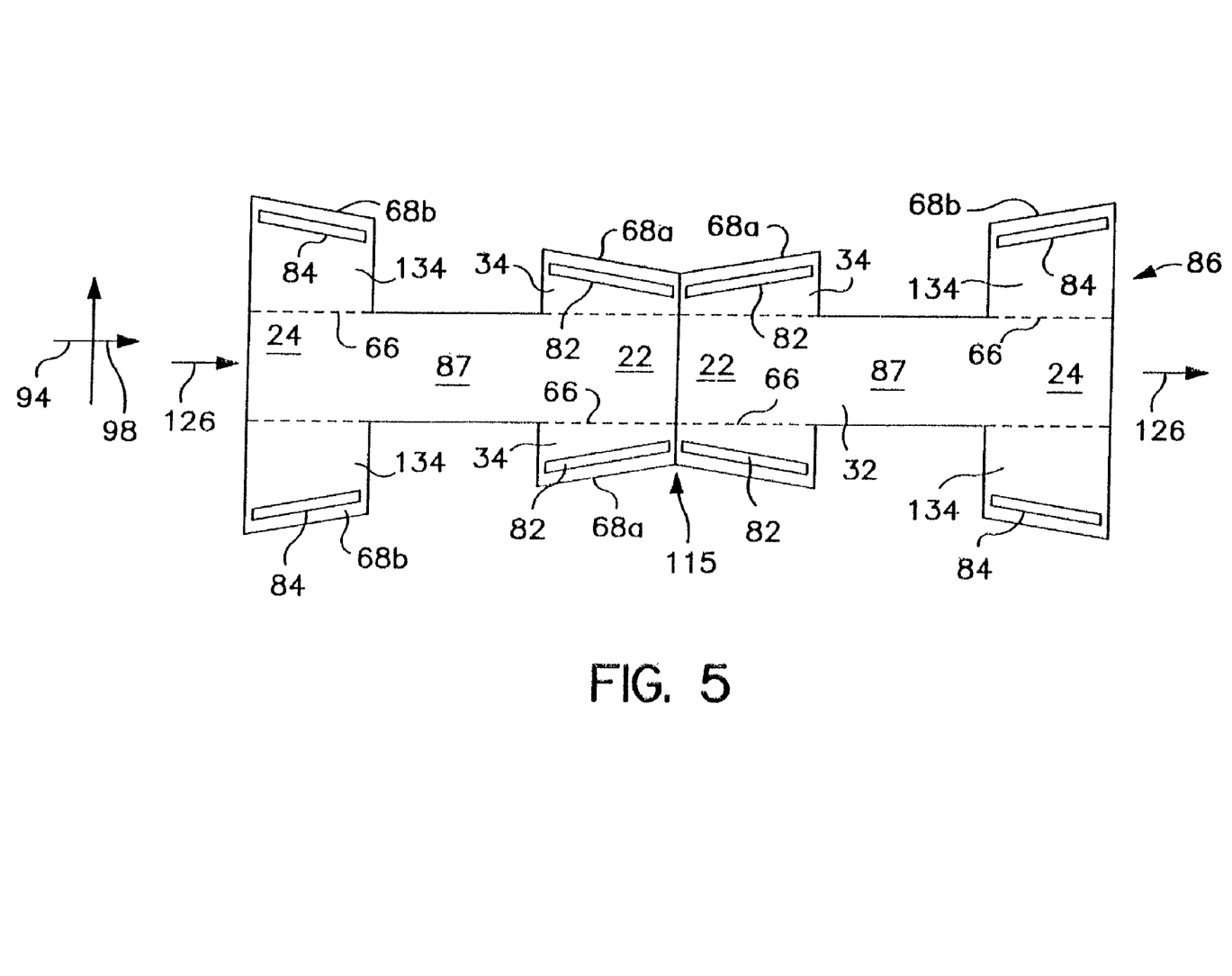
FIG. 5 shows in-process garments according to the present invention still attached to the manufacturing web, with the garments having their longitudinal axes in the machine direction of the web.
Figure 6:
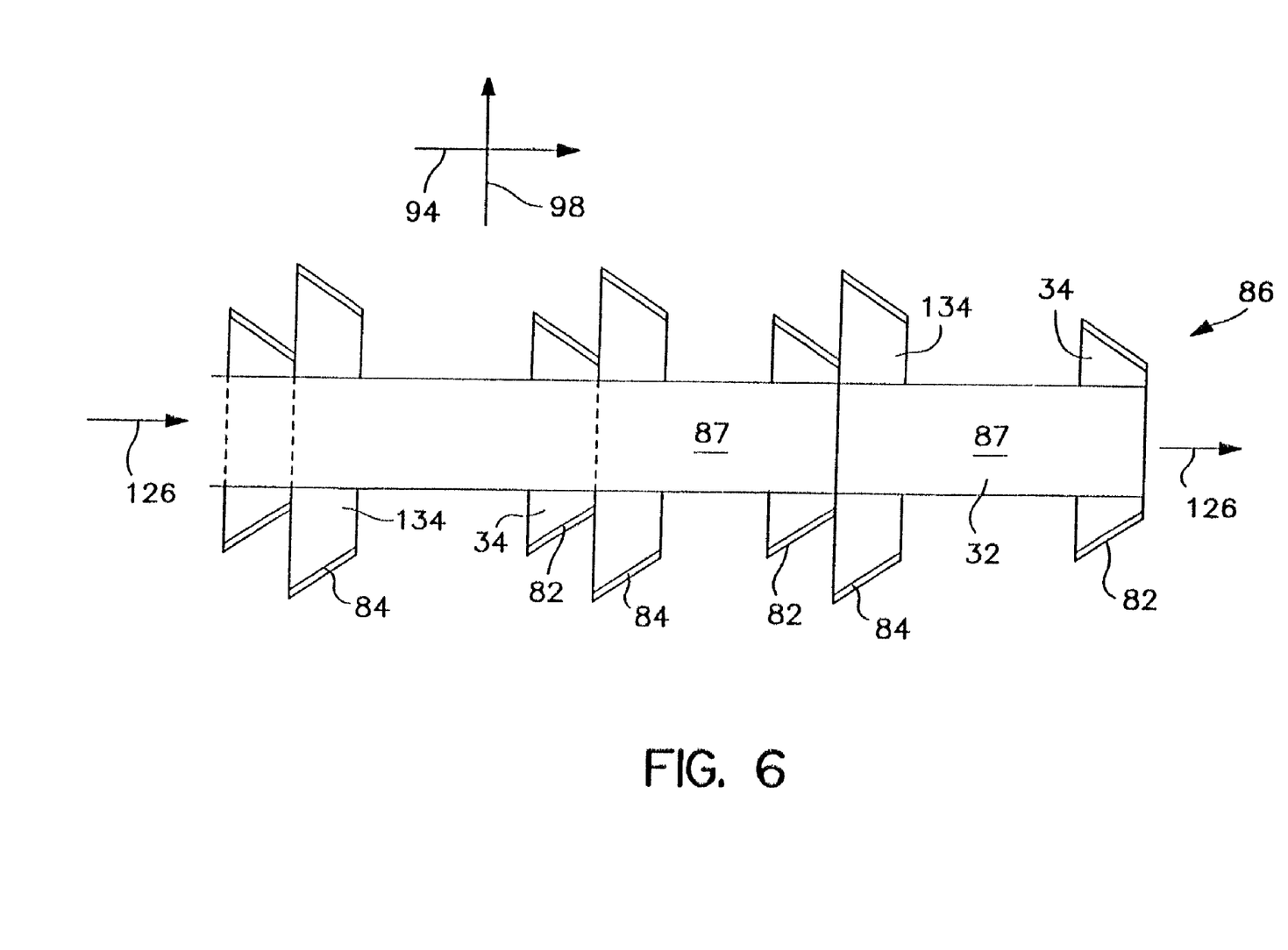
FIG. 6 shows a variant of the machine direction manufacture of FIG. 5.

Referencing FIG. 5, in-process garments 87 are shown as made with their longitudinal axes 126 in the machine direction 94. The side panel portions 34, 134 may be integrally formed from the web of the chassis portion 32 and shaped via cutting or retractive materials, or may be added through securing of a separate side panel web or webs to the chassis web, as by ultrasonic bonding or the like at attachment lines 66. The garments 87 may then be individuated by straight cuts 115 through the web 86 in the cross direction 98. Again, adjacent garments will have mirror image orientation upon individuation although this is not necessary if the manufacturer prefers to have adjacent garments with common orientation, as e.g., in FIG. 6, where the longitudinal axis of the garments 126 extends in the machine direction 94.

Figure 7:
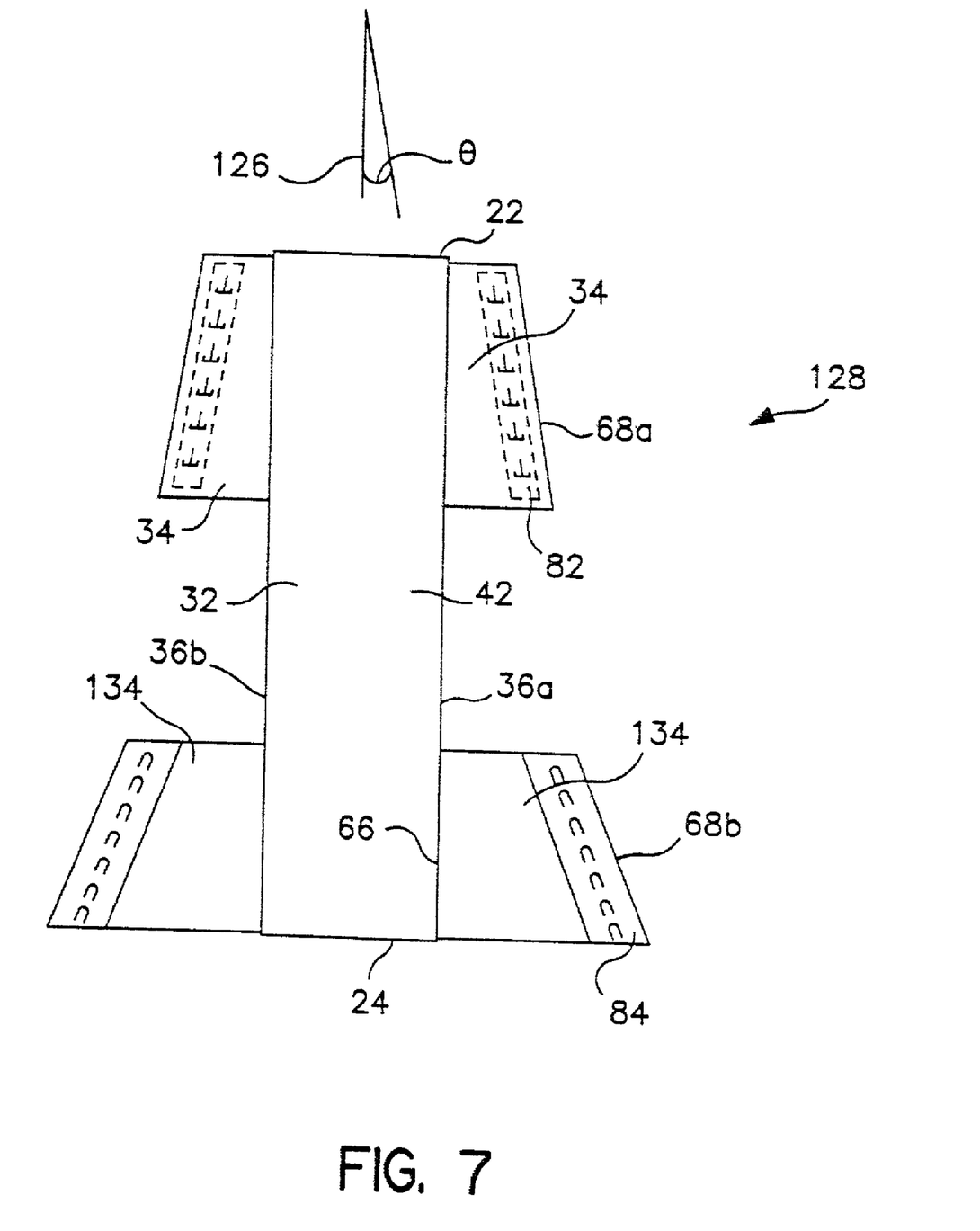
FIG. 7 shows a garment of the present invention in an unfastened laid open state as seen from the interior, or liner, side of the garment and illustrates the angular nature of the side panel distal edges of the present invention.

Referencing FIG. 7, a view of the body side liner, or interior, side 42 of the laid open training pant 20 shows the chassis 32 has front 34 and back 134 side panels secured to, or integral with, both right and left transversely opposed edges 36a, 36b, respectively, of the chassis 32. Only one longitudinal side of the garment will be discussed however for ease of explanation. The distal edges 68a, 68b of the front and back side panels 34, 134, respectively, each define a line, or vector, extending from that edge of the panel proximal the back region 24 to that edge of the panel proximal the front region 22 of the training pant 20 to cross the longitudinal axis 126 of the training pant at an acute angle, $\ominus$, or angles, if the side panel distal edges 68a, 68b are constructed at different angles. The angles made with the longitudinal axis are also congruent within the meaning of the present invention.

The back side panels 134 can be made larger in dimension between their attachment lines 66 and their distal edges 68b than the front side panel 34 in the case of the illustrated training pant 20, although other type garments need not be so configured. The back side panel 134 has secured thereto, on the interior side of the training pant, a strip of loop fastening material 84 shown as running parallel to the distal edge 68b over substantially the entire length of the distal edge. The front side panel 34 has secured thereto, on the outer surface 30 of the training pant, as indicated by phantom outlining, a strip of hook fastening material 82 shown as running parallel to the distal edge 68a over substantially the entire length of the distal edge. While shown as strips, a variety of fastener arrangements will suggest themselves to the artisan.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A disposable pant garment, comprising:
   a garment chassis having a front direction and a back direction;
   a front side-panel and a back side-panel, each extending from the same side of the garment chassis;
   the front side panel and the back side panel each having a waist end edge and a leg end edge and having a distal edge extending from the leg end edge to the waist end edge;
   such that when the garment is laid out flat, each distal edge of each side panel defines a vector extending from one of the waist end edge or the leg end edge along the distal edge of the side panel towards the longitudinal axis of the garment, the vectors of the side panels crossing the longitudinal axis of the garment chassis at congruent angles; and
   at least one of the front side panel and the back side panel being constructed from at least two pieces of material bonded together wherein one piece is proximal to the absorbent chassis and another piece is distal from the absorbent chassis;
   wherein the entirety of the garment is disposable.

2. The disposable pant garment according to claim 1, wherein: the angles defined by the front and back side panel distal edges are acute angles.

3. The disposable pant garment of claim 1, wherein:
   when the garment is laid out flat, the distal edge of the front side panel defining a vector extending from the leg end edge of the front side panel towards the waist end edge of the front side panel;

the distal edge of the back side panel defining a vector extending from the waist end edge of the back side panel towards the leg end edge of the back side panel.

4. The disposable pant garment according to claim 1, wherein: the front and back side panels are engagable at areas proximal their distal edges to create a side seam for the garment;

the side seam having a first terminus at a waist opening of the garment and extending diagonally along a side portion of the garment so as to extend across the side portion to a second terminus at a leg opening of the garment.

5. The disposable pant garment according to claim 4, wherein: the side seam has a line of weakness between front and back side panels.

6. The disposable pant garment according to claim 4, wherein: the front and back side panels are releasably engagable to create the side seam.

7. The disposable pant garment according to claim 6, wherein: the front and back side panels have refastenable fastening components disposed thereon.

8. The disposable pant garment according to claim 7, wherein: the fastening components include hook and loop fasteners.

9. The disposable pant garment according to claim 8, wherein: the hook and loop fasteners comprise strips of hook material and strips of loop material fastened to the side panels parallel and adjacent to the distal edges of the side panels.

10. The disposable pant garment according to claim 9, wherein: the back side panel has a loop fastener.

11. The disposable pant garment according to claim 9, wherein: the front side panel has a hook fastener.

12. The disposable pant garment according to claim 9, wherein: the hook fastener extends from a first surface of the garment.

13. The disposable pant garment according to claim 12, wherein: the loop fastener extends from a second surface of the garment opposite the first surface.

14. The disposable pant garment according to claim 7, wherein: at least one of the refastenable fastening components is integral with a surface of a side panel.

15. The disposable pant garment according to claim 7, wherein: the garment is fastenable by overlapping the back side panel over the front side panel.

16. The disposable pant garment according to claim 1, wherein: the front and back side panels are bonded to the garment chassis.

17. The disposable pant garment according to claim 1, wherein: the back side panel is constructed from at least two pieces of material permanently bonded together.

18. The disposable pant garment according to claim 1, wherein one of the front side panel and the back side panel consists of two members, the members including a first member having the attachment component distal from the garment chassis and a second member proximal the garment chassis and permanently bonded thereto, the two members being bonded together.

19. The disposable pant garment according to claim 1, wherein: the front side panel and back side panel materials have elastomeric properties.

20. The disposable pant garment according to claim 19, wherein: the front side panel and back side panel are elastomeric in a direction transverse to the longitudinal axis of the garment.

21. The disposable pant garment according to claim 19, wherein: the front side panel and back side panel are elastomeric from the waist end edge to leg end edge.

22. The disposable pant garment according to claim 1, wherein: the front side panel and back side panel distal edges for each of a left and right side of the garment are not collinear.

* * * * *